United States Patent [19]

Johnson et al.

[11] 4,064,185

[45] Dec. 20, 1977

[54] OLEFINICALLY UNSATURATED SUBSTITUENTS AT C-11 OF STEROID CYCLIZATION PRECURSORS

[75] Inventors: William S. Johnson, Portola Valley; Grant E. Dubois, Menlo Park, both of Calif.

[73] Assignee: The Board of Trustees of Leland Stanford Junior University, Stanford, Calif.

[21] Appl. No.: 572,378

[22] Filed: Apr. 28, 1975

[30] Foreign Application Priority Data

May 2, 1974 Canada ................................. 198736

[51] Int. Cl.² .............................................. C07C 35/06
[52] U.S. Cl. .......................... 260/617 R; 260/514 L; 260/340.9 AS; 260/586 R; 260/340.7; 260/327 M; 260/526 R; 260/601 R; 260/580; 260/514 G; 260/397; 260/397.3; 260/632 R; 560/203; 560/190; 560/174; 560/205; 560/192
[58] Field of Search ..................................... 260/617 R

[56] References Cited

U.S. PATENT DOCUMENTS

| | | | |
|---|---|---|---|
| 3,741,987 | 7/1973 | Johnson et al. | 260/617 R |
| 3,904,698 | 9/1975 | Johnson et al. | 260/617 R |

OTHER PUBLICATIONS

Johnson et al., J.A.C.S., vol. 93(17), pp. 4332-4334 (1971).
Johnson et al., J.A.C.S., vol. 92(3), pp. 741-742 (1970).

*Primary Examiner*—James O. Thomas, Jr.
*Assistant Examiner*—James H. Reamer
*Attorney, Agent, or Firm*—Townsend and Townsend

[57] ABSTRACT

Compositions are provided as well as methods for preparing the compositions which serve as cyclization precursors for the preparation of C-11 alkenyl substituted steroids and nor-steroids. The alkenyl group may be converted after cyclization to a variety of heterosubstituents to provide heterofunctionalized C-11 steroids and nor-steroids. The compounds are provided having an initiator group, which has a chalcoxy atom in juxtaposition to a double bond, an olefinically unsaturated linking group and a terminating group which acts to from a carbocation which reacts with a nucleophile to provide a stable product. The C-11 substituent is found to provide upon cyclization the alpha-configuration, so that the subject compounds provide a direct route to the difficultly accessible alpha-C-11 substituted steroids, or, if desired, the alpha-configuration can be inverted to the beta-configuration.

2 Claims, No Drawings

OLEFINICALLY UNSATURATED SUBSTITUENTS AT C-11 OF STEROID CYCLIZATION PRECURSORS

The invention described herein was made in the course of work under a grant or award from the Department of Health, Education, and Welfare.

BACKGROUND OF THE INVENTION

1. Field of the Invention

The perhydrocyclopentanophenanthrenes are a widely occurring group of natural substances referred to as steroids. The basic carbon skeleton is retained, with the various steroids differing primarily in the substituents bonded to the annular atoms and the degree and sites of unsaturation.

Depending upon the nature of the substituents, the steroids fulfill a great diversity of functions in both animals and vegetables.

To a great degree, synthetic work in the field of steroids has been dependent upon a source of the intact polycyclic structure, which would then be modified by the introduction, removal or modification of substituents which are present, the introduction or extension of carbon chains, or the like.

The reliance on naturally occurring materials as the substrate for production of commercially useful steroids has many drawbacks. Introduction of a functionality at a particular site may be achieved only with difficulty, where there is no convenient functionality at or near the site of interest. Fluctuations in availability which depend upon the weather, government agencies or the like can make supplies unreliable. Having to rely on naturally occurring materials, reduces the flexibility in being able to introduce new substituents at a variety of sites on the carbocyclic nucleus.

It is, therefore, desirable to be able to synthesize from relatively simple and accessible compounds the steroid nucleus, whereby the substituents are present in the precursor molecules or are introduced by modification of functionalities which are present in the precursor molecules. The synthesis must take into account a number of factors. The steroid nucleus has a specific geometry, so that the synthesis must provide a product which has the desired geometry or one which can be readily modified to achieve the desired geometry. In addition, the product will normally have one or more stereoisomeric sites. Conveniently, the synthesis may allow for resolution of an intermediate, so as to provide for the desired stereoisomer as the final product. Where there is more than one stereoisomeric site, it is desirable that there be asymmetric induction by the stereoisomeric substrate employed in the cyclization process. In addition, each of the steps must anticipate the reagent needs of future steps, so that one minimizes the need for introduction and removal of protective groups, modification of functional groups, and the like. Also, the synthetic procedure must allow for cyclization to the desired product without forming complex mixtures which allow for only difficult isolation of the desired product.

In cyclizing polyenes to polycyclic products, substituents can have both electronic and steric effects. The rather loose aliphatic chain is confined to a rigid orientation as the steroid structure is formed. Substituents may therefore have non-bonded interactions which may impede cyclization. Since the cyclization involves the forming of new bonds from aliphatically unsaturated bonds, olefinically substituents have the opportunity to become involved in the cyclization or enhance the production of undesirable side products.

Description of the Prior Art

Cyclization of monocyclic polyunsaturated compounds has been reported in a number of articles as well as patents. U. S. Pat. Nos. 3,558,672 and 3,598,845 report cyclization of different precursors to the perhydrocyclopentanophenanthrene structure. Scientific artcles of interest include Johnson, et al., J. Am. Chem. Soc., 90 2991 (1968); ibid, 92, 741 (1970); and ibid, 93, 4332 (1971).

SUMMARY OF THE INVENTION

Novel compounds are provided as well as methods for preparing the compounds which may be used in the preparation of steroids having substituents at the C-11 position upon acid catalyzed cyclization. The compounds have an olefinic substituent at the carbon atom which becomes C-11 in the steroid. The synthesis involves linking a group which serves as an initiator having a chalcoxy group in juxtaposition to a double bond, so as to form a new carbon-carbon bond upon acid treatment, an aliphatically unsaturated linking group which has the appropriate geometry to provide the desired ring fusions of the naturally occurring steroids, and a terminating group which forms a carbocation which reacts with a nucleophile to provide a stable product. The intermediates are acylic or long chain substituted carbocyclic compounds, which may be substituted at a number of positions with alkyl groups, particularly at those positions which will be C-10 and C-13 of the resulting steroid.

DESCRIPTION OF THE SPECIFIC EMBODIMENTS

In accordance with this invention, there are provided: intermediates for cyclization to steroidal or nor-steroidal structures; and means for preparing the intermediates. The intermediates are such as to provide a polyenine which has a alkenyl group, particularly an allyl group, at the C-11 position of the steroid. The olefinic substituent may be modified, for example, by oxidation, to introduce heterosubstituents at the C-11 position. The cyclization intermediates are capable of being cyclized under strongly acidic conditions to steroids and nor-steroids without the side chain olefinic unsaturation significantly participating in or diverting the course of the cyclization.

In accordance with this invention, intermediates are prepared which join a polyenine aldehyde, wherein the acetylenic group serves as a terminating group with a phosphonium substituted initiator group to provide a molecule having internally trans olefinic configuration.

The cyclization precursor will normally be of 21 to 44 carbon atoms, more usually of from 23 to 36 carbon atoms, and preferably of from about 23 to 30 carbon atoms, having from 1 to 6 chalcogen atoms, usually 1 to 5 chalcogen atoms, and more usually 1 to 3 chalcogen atoms. Where the chalcogen atoms are solely present in the initiating group, there will frequently be only from 1 to 2 chalcogen atoms in the molecule.

I. Intermediates (The term "chalcoxy," when used in this disclosure, shall mean hydroxy, mercapto, oxyether, thioether, but shall not include esters, peroxides, and higher oxidation states of sulfur, e.g. sulfoxide.)

For the most part, the cyclization precursors will have the following formula:

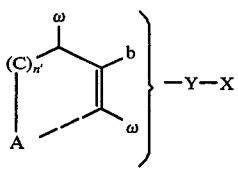

wherein:
one of the omegas (ω) is a bond to —Y—X and is otherwise hydrogen;
b is hydrogen or alkyl of from 1 to 4 carbon atoms, more usually of from 1 to 2 carbon atoms, and usually straight chained;
n' is an integer of from 1 to 2;
A is an alkyl or alkylidene radical (depending on whether the broken line is a bond) of from 1 to 12 carbon atoms, more usually of from 1 to 7 carbon atoms having from 1 to 2 alpha-chalcoxy groups bonded to the carbon atom in the chain and may have an oxygen atom bridging to the adjacent saturated carbon atom to form an epoxide; and
the broken line indicates the presence or absence of a bond, depending upon whether the initiator is cyclic or acyclic.
Y is of from 10 to 20, usually 10 to 18, preferably 10 to 12 carbon atoms, and has the skeletal structure 3,7-decadien-1,10-ylene, and is substituted at the 5-position with an alkenyl group having from 0 to 1 vinyl halo substituents, particularly chloro or bromo, usually 2-alkenyl, and generally of from 2 to 8, usually 2 to 4 carbon atoms, particularly straight chain and preferably 2-halo; and
X is a 1-hydrocarbinyl group, e.g. 1-alkinyl group or phenylethinyl of from 2 to 12, usually 2 to 8, preferably 2 to 6 carbon atoms having from 0 to 1 chalcoxy or carboxyester groups, particularly oxy groups (including carboxy ester) of from 0 to 7, usually 0 to 4 carbon atoms.

The carbon atoms in the parenthesis may be substituted or unsubstituted, when substituted being substituted with alkylidene of from 1 to 4 carbon atoms, more usually of from 1 to 3 carbon atoms, or chalcoxy of from 0 to 6 carbon atoms, more usually of from 0 to 4 carbon atoms, and wherein 2 chalcoxy groups bonded to the same carbon atom may be taken together to form a cyclic ketal of from 5 to 6 annular members, there being a total of from 0 to 2 substitutents on the carbon atoms in the parenthesis.

More particularly, the precursors to the tetracyclic compounds will have the following formula:

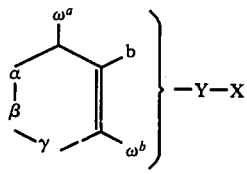

wherein:
the broken line is a bond when the group is cyclic and is not a bond when the group is acyclic;
α is methylene or a bond, being methylene when the broken line is not a bond;
β is alkylidene of from 1 to 8 carbon atoms, usually of from 1 to 6 carbon atoms, more usually of from 1 to 4 carbon atoms having from 0 to 2 alpha-chalcoxy groups, wherein the two chalcoxy groups may be taken together to form a cyclic ketal of from 5 to 6 annular members, and having from 0 to 1 site of ethylenic unsaturation, or with the proviso that the broken line is a bond, of the following formula $\omega^c$—CH< ;
γ is alpha-chalcoxyhydrocarbyl having from 1 to 2 alpha-chalcoxy groups and being of from 1 to 10 carbon atoms, more usually of from 1 to 8 carbon atoms and free of aliphatic unsaturation and includes alkyl, cycloalkyl and phenyl substituents on the carbon atom in the chain, and wherein an oxygen atom may bridge to β to form an epoxy group;
when the broken line is a bond, γ is usually alkylidene of from 1 to 6 carbon atoms, more usually of from 1 to 4 carbon atoms and having from 1 to 2 alpha-chalcoxy groups which may be taken together to form a cyclic ketal of from 5 to 6 annular members, and when the broken line is not a bond, γ will be hydrocarbyl having from 1 to 2 alphachalcoxy groups which may be taken together to form a cyclic acetal or ketal of from 5 to 6 annual members and is of from 1 to 8 carbon atoms, more usually of from 2 to 8 carbon atoms and free of aliphatic unsaturation, and wherein one of the chalcoxy groups may be taken together with β to form an epoxide ring;
b is hydrogen or lower alkyl of from 1 to 4 carbon atoms, more usually of from 1 to 3 carbon atoms, and preferably of from 1 to 2 carbon atoms and is straight chained; and
$\omega^{a-c}$ is a bond to Y and is otherwise hydrogen;
Y is 5-e-7-a-3,7-decadien-1,10-ylene, where the 1-position is bonded to Z and the 10-position is bonded to X and is of the formula:

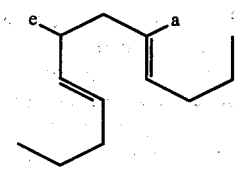

wherein:
a is hydrogen or lower alkyl of from 1 to 4 carbon atoms, usually of from 1 to 3 carbon atoms and preferably of from 1 to 2 carbon atoms, particularly methyl, and usually straight chained;
e is β-alkenyl of from 3 to 6 carbon atoms, more usually of from 3 to 4 carbon atoms, and preferably 3 carbon atoms, β-halo-β-alkenyl of from 3 to 6 carbon atoms, usually of from 3 to 4 carbon atoms, and more usually 3 carbon atoms, the halo being of atomic number 17 to 35 (chloro and bromo); and
X is of the formula:

wherein:

g is hydrogen, hydrocarbyl of from 1 to 10 carbon atoms, chalcoxy hydrocarbyl of from 1 to 10 carbon atoms, or acylcarboxy hydrocarbyl of from 1 to 10 carbons, particularly alpha; when aliphatic, lower alkyl of from 1 to 4 carbon atoms, when chalcoxy hydrocarbyl, particularly alpha-chalcoxyalkyl of from 1 to 8 carbon atoms, more usually of from 1 to 4 carbon atoms, and particularly hydroxyalkyl of from 1 to 2 carbon atoms, preferably hydroxymethyl, or acylcarboxyalkyl of from 1 to 8 carbon atoms, more usually of from 1 to 4 carbon atoms, and preferably acetoxymethyl wherein the acyl group is free of unsaturation; when aromatic, phenyl, alkylphenyl of from 7 to 10 carbon atoms and chalcoxyphenyl of from 6 to 10 carbon atoms.

Illustrative Z groups include:
1-hydroxy-1-ethylcyclopent-2-en-2-yl;
trimethylene dithoketal of 6-hydroxy-5-oxo-2-ethyl-cyclohex-1-en-1-yl;
2-hydroxy-2-ethylcyclopent-3-en-1-yl;
2,3-butylene ketal of 6-hydroxy-5-oxo-2-methyl-cyclohex-1-en-1-yl;
6-hydroxy-5-isopropylidenyl-2-methyl-cyclopent-1-en-1-yl;
ethylene dithioketal of 2-ethyl-6-oxocyclohex-1-en-1-yl;
2,3-butylene dithioketal of 2-ethyl-4-oxocyclohex-2-en-1-yl; and
2-ethyl-5-hydroxy-5-methylcyclopent-1-en-1-yl.

Illustrative Y groups include:
5-(2'-bromoprop-2'-yl-1')-7-ethyldeca-3,7-dien-1,10-ylene;
5-(but-2'-enyl-1')-7-methyldeca-3,7-dien-1,10-ylene;
5-(-2'-chloro-2'-chloro-2'-buten-1'-yl)-7-methyldeca-3,7-dien-1,10-ylene;
5-(pent-2'-enyl-1')-7-ethyldeca-3,7-dien-1,10-ylene;
5-allyl-3,7-dien-1,10-ylene; and
5-(3'-chloroallyl)-3,7-dien-1,10-ylene.

Illustrative X groups include:
prop-1-in-1-yl;
3-hydroxyprop-1-in-1-yl;
3-methoxyprop-1-in-1-yl;
3-hydroxybut-1-in-1-yl;
3-ethoxyprop-1-in-1-yl;
3,4-dimethoxybut-1-in-1-yl;
3-benzyloxyprop-1-in-1-yl;
2-phenylethinyl;
2-p-phenetylethinyl; and
2-benzylethinyl.

For the most part, the cyclic compounds of this invention will have the following formula:

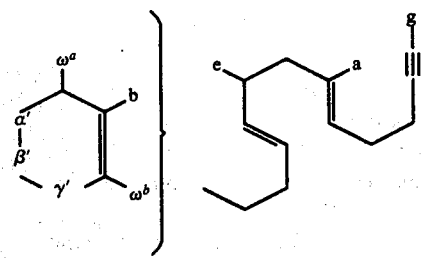

wherein:
a and b are hydrogen or alkyl of from 1 to 4 carbon atoms, more usually of from 1 to 3 carbon atoms, and preferably of from 1 to 2 carbon atoms, particularly methyl, with a preferably being alkyl;
g is alkyl, having from 0 to 1 chalcoxy or acylcarboxy group, i.e. chalcoxyalkyl, or acylcarboxyalkyl, particularly alkyl and oxalkyl of from 1 to 8 carbon atoms, more usually of from 1 to 6 carbon atoms, preferably of from 1 to 4 carbon atoms, particularly preferred of from 1 to 2 carbon atoms, particularly methyl and hydroxymethyl, or carbocyclic aryl of from 6 to 12, usually 6 to 10 carbon atoms, having from 0 to 2, usually 0 to 1 chalcoxy substituents or carboxyester substituents;
e is 2-alkenyl-1 of from 3 to 6 carbon atoms, more usually of from 3 to 4 carbon atoms, and preferably 3 carbon atoms, having from 0 to 1 halo atom of atomic number 17 to 35 at the 2-position;
$\alpha'$ is a bond or methylene;
$\beta'$ is alkylidene of from 1 to 8, more usually of from 1 to 6, and preferably of from 1 to 4 carbon atoms, having from 0 to 2 alpha-chalcoxy groups bonded to the annular carbon atom, wherein 2 chalcoxy groups may be taken together to form a cyclic ketal of from 5 to 6 annular members, and having from 0 to 1 site of ethylenic unsaturation, particularly exo unsaturation, that is, a double bond to the annular carbon atom, or of the formula:

$\gamma'$ is alpha-chalcoxyalkylene of from 1 to 8, more usually 1 to 6, and preferably 1 to 4 carbon atoms, having from 1 to 2 chalcoxy groups bonded to the annular carbon atom, wherein 2 chalcoxy groups may be taken together to form a cyclic ketal of from 5 to 6 annular members; and
wherein one of $\omega^{a-c}$ is a bond, but are otherwise hydrogen.

When Z is acyclic, the compounds for the most part will have the following formula:

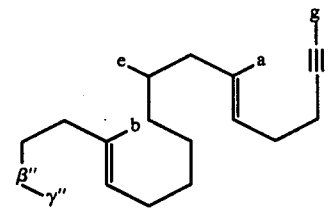

wherein:
a, b, e and g have been defined previously;
$\beta''$ is an aliphatic hydrocarbylidene group having from 0 to 2 alpha-chalcoxy substituents and from 0 to 1 site of ethylenic unsaturation, particularly $\Delta^1$ and is of 1 to 8 carbon atoms, more usually of from 1 to 6 carbon atoms, and preferably of from 1 to 4 carbon atoms, and usually methylene and may be taken together with $\gamma''$ to form an epoxide ring; and
$\gamma''$ is chalcoxymethyl of from 1 to 12 carbon atoms, more usually of from 1 to 10 carbon atoms, preferably of from 1 to 8 carbon atoms, and more preferred of from 1 to 5 carbon atoms, having from 1 to 2 alpha-chalcoxy groups, where 2 alpha-chalcoxy groups may be taken together to form a cyclic ketal of from 5 to 6 annular members and one chalcoxy group may be taken together with $\beta''$ to form an epoxide ring; $\gamma''$ may be substituted with aliphatically saturated hydrocarbyl groups—alkyl, cycloalkyl, or carbocyclic aryl groups—of from 1 to 8 carbon atoms, more usually of from 1 to 6 carbon atoms and when other than aryl, of from 1 to 2 carbon atoms, particularly methyl.

The phosphonium salt which is employed in the Schlosser-Wittig condensation and provides the initiator group will for the most part have the following formula:

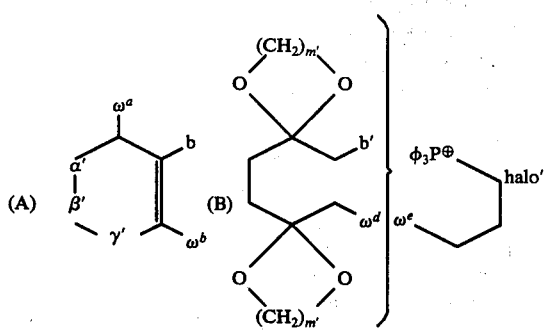

wherein:
all of the symbols except as follows have been defined previously:
$b'$ is hydrogen or alkyl of from 1 to 3 carbon atoms;
$m'$ is of an integer of from 2 to 3;
halo$'$ is halogen of atomic number 17 to 53; and one of $\omega^{a-d}$ is a bond with $\omega^e$.

Thus, the formulas designated by A and B are Z or are used in the formation of Z as indicated for Z$'$.

The terminator portion of the molecule, which also carries the alkenyl substituent, will for the most part have the following formula:

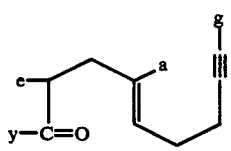

wherein:
$a$, $e$ and $g$ have been defined previously; and
$y$ is hydrogen or hydroxyl. When hydroxyl, the compound can be resolved into its stereoisomers, $d$ or $l$.

II. Methods of Preparing Intermediates

The intermediates described in Section I are prepared by the condensation of two units which provides for the $\Delta^3$ double bond of Y. The double bond is conveniently introduced by condensation between a phosphonium ion and an aldehyde under Schlosser-Wittig conditions, whereby the double bond which is formed is predominantly trans. The trans configuration is the natural configuration of the steroid product at this ring fusion and, therefore, on cyclization, the desired geometry at the ring fusion is obtained.

The preparation of the various fragments, which contain the Z group for condensation with the aldehyde, has appeared in a number of references and will be further disclosed in the experimental section. The following publications are therefore cited to demonstrate the synthesis of a number of different Z group containing fragments.

Johnson, Accounts of Chem. Research, 1968, 1; Johnson, et al., J. Am. Chem. Soc., 90, 299 (1968); Johnson and Schaaf, Chemical Comm., 1969, 671; Abrams, et al., Bioorganic Chemistry, 1, 243 (1971); Johnson, et al., J. Am. Chem. Soc., 93, 4332 (1971); Johnson, et al., ibid, 92, 4461 (1972). U.S. Patents Nos. 3,558,672 and 3,598,845 and German Offenlegungsschrift P22 34 018.7 and P24 18 877.0.

The Schlosser-Wittig reaction combines in an ethereal solvent approximately equimolar amounts of the ylide, particularly the triphenylphosphonium ylide, with the appropriate aldehyde. An ethereal solvent is employed, e.g. tetrahydrofuran, diethyl ether, dimethoxyethylene and combinations thereof. The temperature will normally be about $-90°$ to $-50°$ C and the concentration of reactants will generally be from about 0.05 to 1M, usually from about 0.1 to 0.5M. Carbocyclicaryl lithium, e.g. phenyl lithium is added in at least about equimolar amount and usually in excess, ranging from about 1 to 2 moles per mole of ylide-aldehyde reactant. The temperature is allowed to rise to from about $-50°$ to $-10°$ C and after a sufficient time, e.g. 5 min to 1 hour, the reaction is quenched, e.g. by addition of a lower alkanol, for example, methanol. The product may then be isolated and purified according to conventional procedures.

See also the following articles: J. A. C. S., 95, 2656 (1973); ibid, 94, 8225, 8228, 8229 (1972); J. Chem. Soc., 1131 (1957); J. Org. Chem., 36, 1137 (1971); J. A. C. S., 93, 4330 (1971); and J. Org. Chem., 27, 1615, 1620 (1962). The methods described in these articles may require some modification for producing a specific Z group, such as condensation of methyllithium with a ketone, to form a tertiary hydroxy group, reduction of the ketone to an alcohol, or the like. By preparing the appropriate haloalkyl substituted cyclohexene, the haloalkyl cyclohexene may be condensed with triphenylphosphine and by addition of phenyllithium, the phosphonium salt may be condensed with the appropriate aldehyde to provide the precursor to the polycyclic compound. The following chart indicates the reaction sequence.

Chart 1

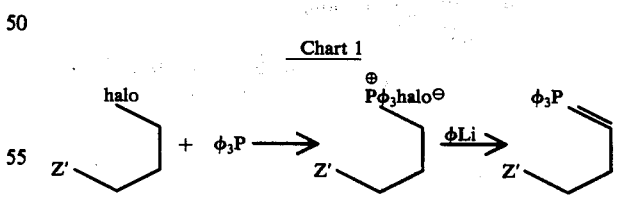

wherein Z$'$ is the same as Z or a group which by modifications indicated previously will form Z after the condensation with the aldehyde and halo intends halogen of atomic number 17 to 53, particularly 17 to 35.

The next sequence of reactions is found in Chart 2, which involves an exemplary preparation of alkenyl substituents at the C-11 carbon atom, with preparation of the C-11 substituted progesterone and chemical modification of the C-11 substituent.

Chart 2
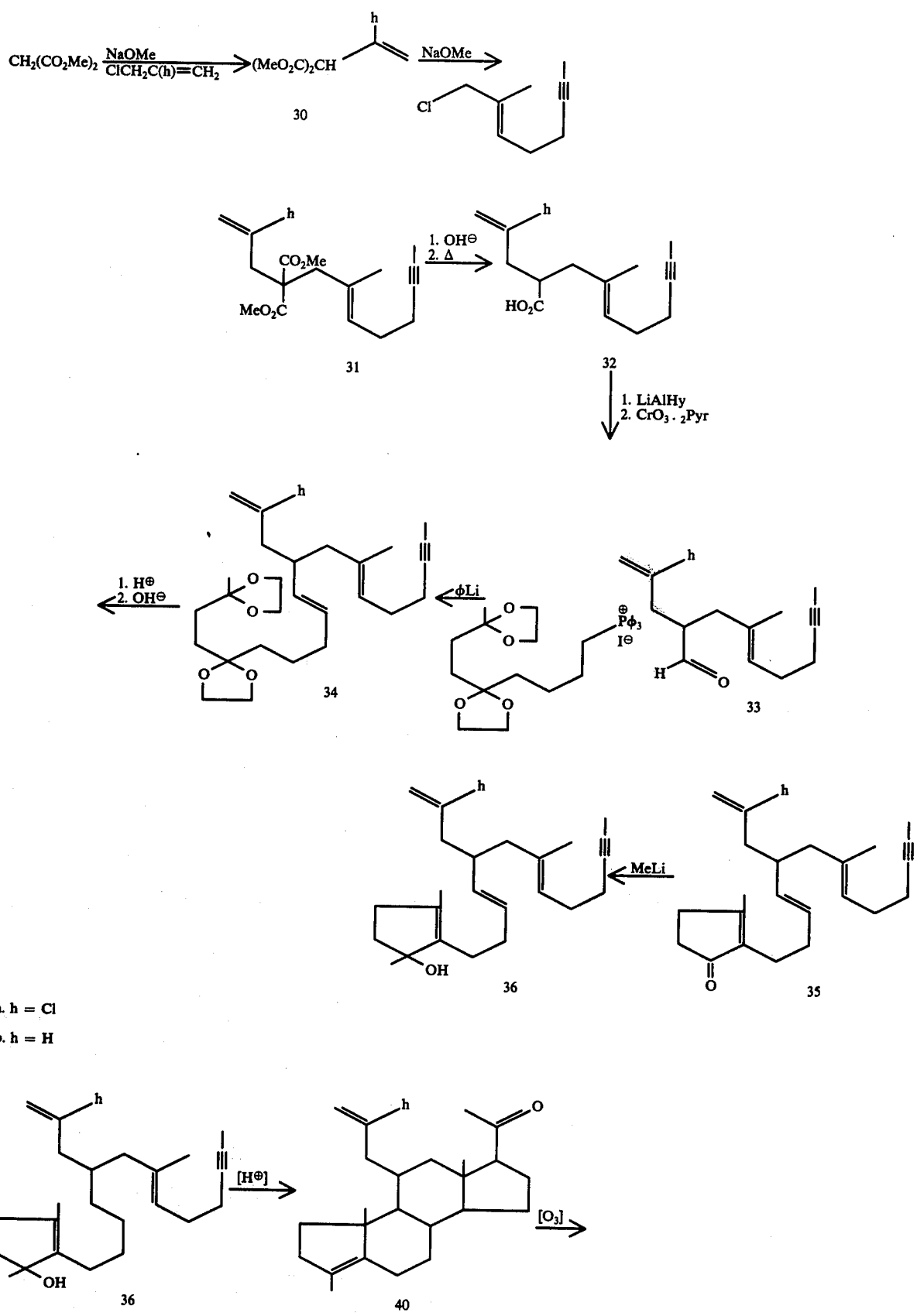
a. h = Cl
b. h = H

-continued
Chart 2

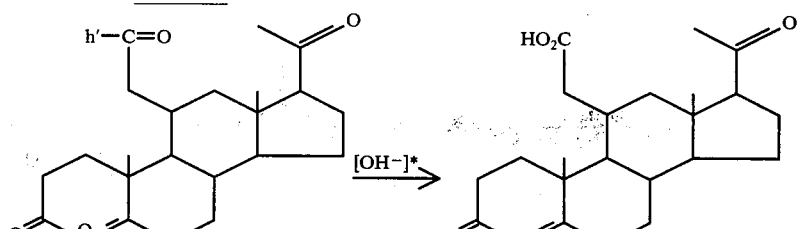

41 42 h = H; h' = H
h = Cl; h' = OH
*when h' = H, the aldehyde is oxidized prior to base treatment In Chart 2, h is halogen of atomic number 17 to 35, preferably chloro, or hydrogen.

In accordance with the subject invention, polyenyne compounds are prepared which have the desired geometry, so that on cyclization the steroidal product has the naturally occurring configuration. During the course of the reaction, the double bonds, which are introduced, are introduced in such a manner as to provide the necessary geometry, without affecting the geometry of the substituents. In addition, the precursor having the C-11 substituent may be resolved to the desired stereoisomer, so that on cyclization, by virtue of asymmetric induction, the naturally occurring product may be obtained directly without further separation. Thus, the synthetic procedure provides routes to a cyclization precursor or intermediate which allows for great flexibility in the introduction of various substituents, both hydrocarbon and hetero at a variety of positions, particularly C-10, C-11, C-13 and C-17.

III. Cyclization

The cyclization of the polyunsaturated substituted carbocyclic ring is catalyzed by a strong acid, usually carboxylic, particularly a halocarboxylic acid having halo at the α-position, and more particularly, a perhalocarboxylic acid, usually chloro or fluoro, preferably fluoro and of from 2 to 4 carbon atoms, particularly 2 carbon atoms. For the most part, carboxylic acids are employed having a pK at 25° C of less than about 4.

The solvent is a protic solvent, particularly an organic chalcoxy solvent, e.g. hydroxylic solvent of from 2 to 4 carbon atoms, preferably 2 carbon atoms, preferably a halochalcoxy solvent, e.g. a haloalkanol, wherein the halogen is of atomic number 9 to 17, particularly fluoro and chloro, and more particularly fluoro, and having at least one halogen atom per carbon atom, preferably at least 1.5 halogen atoms per carbon atom—a fraction being taken to the next higher number—and particularly preferred trifluoroethanol, wherein halogen is on other than the carbon atom bonded to the hydroxyl.

Small amounts (<25 vol. %, usually <15 vol. %, based on the total volume of the reaction mixture) of other inert solvents may be employed, which are miscible with the major solvent. Inert halohydrocarbons, e.g. methylene dichloride, fluorochloromethane, dichloroethane, etc. may be added of from 1 to 3 carbon atoms and 1 to 8 halogen atoms, particularly fluorine and chlorine. Water may also be present, not only from the dehydration of the substrate but also adventitiously present in small amounts where the intermediate product has not been dried.

The reaction will normally be carried out in an inert atmosphere at temperatures in the range of about −10° to 40° C, usually −5° to 30° C, and preferably from about −5° to 25° C, and more preferably 0° to 25° C. The time for the reaction will vary widely, but will be at least about 10 minutes and may be two weeks or more, usually being at least about 0.5 hour, and generally not more than 96 hours, but at least the minimum time to provide the desired yield. Ambient pressures are normally satisfactory.

The concentration of the reactant based on solvent (not including the acid catalyst) will generally range from about 0.001M to about 0.1M, more usually from about 0.005M to 0.05M. While the concentration is not critical, relatively dilute solutions will be employed to minimize the opportunity for polymerization.

The mole ratio of the acid to the cyclization substrate may also be varied quite widely. Normally, at least about 5 moles of the carboxylic acid will be employed per mole of substrate, more usually at least 10, and generally not more than about 750 moles, more usually not more than about 500 moles of carboxylic acid, per mole of cyclization substrate.

The molar concentration of the acid catalyst will generally be from about 0.5 to 15M, more usually about 1 to 10M, and preferably about 2 to 5M. Increasing molarity is desirable to enhance the yield of the desired product.

The order of addition is not critical. The acid may be added to the substrate in solution or the substrate may be added to the acid in solution. Normally, the acid and substrate will not be combined except in the presence of solvent.

Depending on the solvent system and acid reagent, various moieties will serve as the nucleophile. In the presence of water, both the water and acid may compete for the carbocation. Various other molecules may be present which are capable of forming a stable covalent bond with the carbocation. With the vinyl carbocation being captured by water, oxo will be formed directly. Otherwise, vinyl esters and ethers may be isolated. These may then be hydrolyzed to the C-20 oxo group.

The workup may follow conventional techniques, whereby the acid is neutralized with a mild base and the product extracted by any convenient solvent. The product may then be purified by any convenient preparative means such as chromatography, solvent-solvent extraction, etc.

IV. Tetracyclic Products

The cyclic products, which are formed in accordance with the subject invention, will have from about 20 to 45 carbon atoms, usually from about 20 to 36 carbon atoms, and more usually from about 21 to 36 carbon atoms, generally having from about 21 to 30 carbon atoms when X is propargyl and from about 25 to 35 carbon atoms, when X is phenylethinyl.

For the most part, the tetracyclic compounds formed by the subject cyclization will have the following formula:

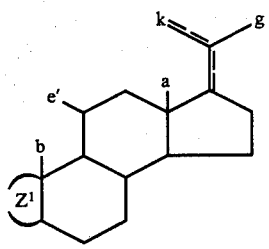

wherein:

a, b and g have beed defined previously, e' is the same as e, and $Z^1$ is a di- or trivalent organic radical which forms a ring of from 5 to 6 annular members with the carbon atoms to which $Z^1$ is attached and has from 0 to 2 chalcoxy groups or 0 to 1 oxo group and has from 1 to 2 sites of ethylenic unsaturation, there being 1 endo-double bond, which may be subsequently hydrogenated. When $Z^1$ is trivalent, there is a double bond to a bridgehead carbon atom. $Z^1$ is normally of from about 3 to 9 carbon atoms, usually of from 3 to 7 carbon atoms, and preferably of from about 4 to 7 carbon atoms and 0 to 2 chalcogen atoms. There is one double bond between the carbon atoms and k signified by the broken line. When the double bond is between the carbon atoms, k is a carboxy ester of from 2 to 4 carbon atoms and 1 to 6 halogen atoms of atomic number 9 to 17, e.g. trifluoroacetoxy, while when the double bond is between the carbon atom and k, k is oxygen.

Illustrative $Z^1$ groups include:
but-1-en-1,4-ylene;
3-methylprop-1-yl-3-ylidene;
2-(2'-thiolethylenethio)but-1-en-1,4-ylene;
3-isopropylidenebut-1-yl-4-ylidene;
3-ethylprop-1-yl-3-ylidene; and
3-oxobut-1-yl-4-ylidene.

When the cyclization is carried out with a cyclopentenol compound, the resulting product will for the most part have the following formula:

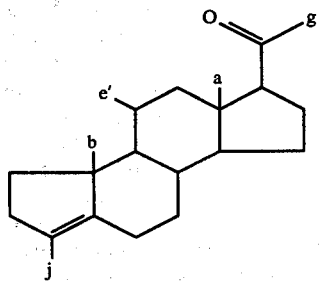

wherein:

a, b, e' and g have been defined previously, and j is hydrogen or alkyl of from 1 to 4 carbon atoms, usually of from 1 to 2 carbon atoms, and more usually methyl.

Upon oxidation of the endocyclic double bond, for example, ozonization, the ring is opened to a diketone. In addition, if a substituent at C-11 has aliphatic unsaturation, that double bond will also be cleaved to provide an aldehyde or carboxylic acid. The product of oxidation will have the following formula:

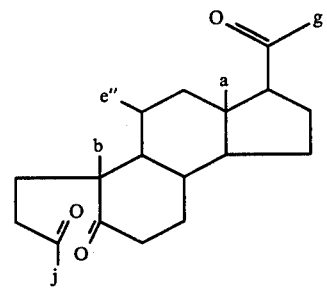

wherein:

a, b, g and j have been defined previously, and e'' is formylmethyl or carboxymethyl.

When j is other than hydrogen upon base catalyzed condensation, the A ring is reformed to form a product of the following formula:

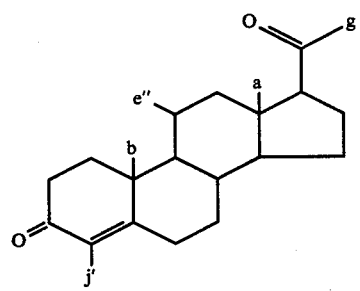

wherein:

a, b, e'', usually carboxymethyl, and g have been defined previously, and j' is hydrogen or alkyl of from 1 to 3 carbon atoms, usually of 1 carbon atom and preferably hydrogen.

Where the initiator is a cyclohexenyl group, the resulting product will for the most part have the following formula:

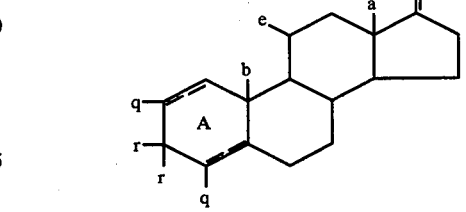

wherein:

a, b, e, k and g have been defined previously;
the meaning of the broken line between C-17 and C-21 has been defined previously;
one of the broken lines in the A ring is a double bond, particularly $\Delta^1$,
the q bonded to the ethylenic carbon atom is H or β or γ hydrochalcoxy-(OH or SH)-alkylenechalcoxy (alkylene of 2 to 3 carbon atoms), the other q is hydrogen; and the two r's are hydrogen or may be taken together to form alkylidene of from 1 to 4 carbon atoms, a cyclic oxy or thio ketal or oxo.

Depending on the other Z groups involved, various transformations of the functionalities present in the Z group will be appropriate. Ketones can be reduced to alcohols, double bonds introduced into the ring, exocyclic double bonds cleaved by ozonization and the like.

The cyclization provides the substituted steroids at the C-11 with the alpha-configuration. Since this configuration has shown physiological activity in steriod derivatives, the fact that it is obtained directly without the presence of significant amounts of the beta-configuration allows for direct synthesis to the alpha-configuration without the need to separate mixtures of the two isomers. In addition, since the intermediates can be resolved at an early stage, the alpha-C-11 isomer can be provided optically active.

EXPERIMENTAL

The following examples are offered by way of illustration and not by way of limitation.

(All temperatures not otherwise indicated are in Centigrade. All percents not otherwise indicated are by weight. The phrase "worked up in the usual manner" means the organic layer is washed with brine, dried over anhydrous magnesium sulfate, filtered, and the solvent removed in vacuo. Where a number is indicated with a compound, it relates to the number in an earlier chart or a number independently given.)

EXAMPLE 1 a. 3-Carboethoxy-6-chlorohept-5-en-2-one (cis/trans).

To a solution of 46g sodium (2g atom) in 500ml ethanol at reflux, in a 2-liter flask equipped with mechanical stirrer, and addition funnel, was added 325g ethyl acetoacetate (2.5 mole) over 30 minutes. The resulting solution of enolate was refluxed for 15 minutes, and then 250g (2.0 mole) 1,3-dichlorobut-2-ene was added dropwise at such a rate as to maintain reflux with gentle heating towards the end of the addition. After addition, refluxing and stirring were maintained for 4 hours, the condenser converted for distillation, and ethanol removed as 500ml distillate. The residual product was cooled, water and 1.2N hydochloric acid were added and the organic layer separated. The aqueous portion was extracted with ether, the organic layers combined, washed with water and brine, filtered through sodium sulfate and evaporated in vacuo to give 485g dark yellow oil (96%, based on dichlorobutene). Vpc showed 73% of trans plus cis product, together with other volatiles.

b. Methyl 4-hexynoate.

Crude 3-carboethoxy-6-chlorohept-5-en-2-one from part (a) above, (242g) was added dropwise (at such a rate as to maintain reflux) to 264g (4 mole) 85% potassium hydroxide dissolved in 250ml 95% ethanol in a 2-liter 3-necked flask equipped with mechanical stirrer, reflux condenser and addition funnel. After the addition the condenser was converted for distillation, 150ml ethylene glycol and 50ml 2-ethoxyethanol were added, and ethanol/water distilled off until the pot-temperature had reached 130°-135°. Stirring and heating under reflux were continued for 5 hours at 130°-135°, the reaction mixture cooled to about 80°, one liter brine added, the mixture stirred for 2-3 hours at room temperature and then poured into a separatory funnel. After washing with ether (3 × 150ml), the aqueous solution was then acidifed with cold concentrated hydrochloric acid to pH 6.5, extracted with chloroform, acidified to pH 1.0, and again extracted with chloroform. The pH 1.0 extracts were washed with 200ml brine, filtered through sodium sulfate and evaporated in vacuo to give 67.1g (60% based on dichlorobutene) pale brown crystalline solid (after removal of acetic acid by azeotroping with 1,4-dioxan and vacuum drying). A small sample of the acid was purified by crystallization from benzene: pentane and vacuum sublimation to give 4-hexynoic acid, colorless needles, m.p. 99°-100°.

The crude acid was dissolved in 150ml dry methylene dichloride and 48g methanol, and refluxed for 20 hours with 0.50g p-toluenesulfonic acid monohydrate. The reaction mixture was cooled, diluted with saturated sodium bicarbonate solution, separated and the aqueous layer extracted with ether. The combined organic extracts were washed with saturated sodium bicarbonate solution and the product isolated to give 58g orange oil. Distillation in vacuo through a small Vigreux column gave 51.0g methyl 4-hexynoate as colorless oil, b.p. 77°-78°/21mm.

c. 4-Hexynal

4-Methyl hexynoate (25.0g, 0.20 mole) was dissolved in 100ml dry tetrahydrofuran in a 500ml flask equipped with mechanical stirrer and addition funnel with provision for "Dry-Ice"/acetone cooling. To the stirring solution at −70° under dry $N_2$ was added over 1 hour, 70ml of a 3.54M solution of sodium bis(2-methoxyethoxy)aluminum hydride (Redal) in benzene diluted to 140ml (total volume) with dry tetrahydrofuran from the cooled addition funnel. The product was then stirred for 5 hours at −70° and then 14.2ml (11g, 0.25 mole) acetaldehyde, was added slowly by syringe. After 10 minutes at −70° the reaction mixture was poured into a mixture of 100ml concentrated hydrochloric acid and 500ml saturated brine. The mixture was ether extracted and the extracts washed with 50ml saturated sodium bicarbonate solution and with 50ml brine, then filtered through $Na_2SO_4$ and evaporated in vacuo at RT. The crude 4-hexynal was used directly for the next step after drying over "4A"-molecular sieves to remove ethanol.

d. 2-Methyloct-1-en-6-yn-3-ol, 6a

Magnesium (14.4g, 0.6g atom) was dried in a 250ml flask fitted with reflux condenser, mechanical stirrer and addition funnel. After initiation of reaction under dry $N_2$ with about one ml ethylene dibromide in 70ml tetrahydrofuran, 36.0g (0.30 mole) 2-bromopropene was added dropwise at such a rate as to maintain reflux without external heating. The Grignard solution was then stirred until it cooled to room temperature (30 minutes-1 hour). It was then cooled further to −15° in ice-salt, and the total crude 4-hexynal from part (c) above was added dropwise over 15 minutes. The reaction mixture was stirred for 2 hours at room temperature, saturated ammonium chloride solution was added and the product was extracted with ether. There was obtained 23.50g of (2-methyloct-1-en-6-yn-3-ol (85%, based on 4-methyl hexynoate) as a pale yellow oil.

Apart from small samples for characterization, the alcohol was rather unstable to distillation or chromatography, and was used crude in the next step for best overall yields.

EXAMPLE 2 1-Chloro-2-methyloct-2-en-6-yne, 7a

A mixture of 3-hydroxyoct-1-en-6-yne 6 (0.73g, 5.26 mmoles, dry to $MgSO_4$) in hexane (dry to $Al_2O_3$, 15 ml)

and thionylchloride (1.36ml, fresh-dried from $P(OEt)_3$) was heated to 52° under $N_2$ for 2.2 hour. The excess thionyl chloride was removed under reduced pressure (rotary), leaving a dark residue. The residue was dissolved in hexane (50ml) and the organic phase washed with water (twice, 15ml each), bicarbonate (twice, 15ml each) and brine (once, 25ml). Evaporation of the dried ($MgSO_4$) organic phase yielded a brown liquid, which was chromatographed on Florisil (40g, Fisher, 100–200 mesh, hexane elution). The combined chloride fractions were distilled (110° at 1.0mm, Kugelrohr) affording the primary chloride 7 (0.51g, 62%) contaminated with isomeric secondary chloride.

EXAMPLE 3 1-Chloro-2-methyl-2trans-octen-6-yne, 7a

A mixture consisting of 85% of 1-chloro-2-methyl-2trans-octen-6-yne and 15% of 3-chloro-2-methyl-1-octen-6-yne (3.2g) was fractionated in a small spinning band apparatus (Nester Faust, microstill) at 9mm. When the pot residue was shown to contain the desired less volatile trans isomer in greater than 98% purity, the distillation was interrupted, and the residue was freed from some black junk by bulb-to-bulb distillation at 120°/9mm.

CHART 2 EXAMPLES

EXAMPLE 4
Dimethyl-2-(2-chloropropenyl)-malonate, 30a

A solution of 0.20 mole NaOMe in MeOH was prepared by rapidly adding 4.60g (0.20 mole) of sodium metal to 100ml of absolute MeOH while stirring under dry nitrogen in a flame-dried 250ml three-necked flask. When NaOMe formation was complete, the base solution was heated to 50°, after which 27.7g (0.21 mole) of dimethyl malonate was added dropwise over 5 minutes. After 5 minutes, 22.0g (0.20 mole) of 2,3-dichloropropene was added dropwise over 10 minutes. A very vigorous reaction occurred precipitating NaCl. Following addition, the reaction mixture was refluxed for 60 minutes. Concentrated HCl was then added to neutralize the solution and the solvent was evaporated. The residue was taken up in 50ml of ether and 50ml water. The aqueous solution was washed with ether (2 × 25ml) and the combined ether extracts were washed with brine, dried over $MgSO_4$ and concentrated yielding 38.0g of a light yellow liquid. Vacuum distillation through a 30cm Vigreux column yielded 19.46g of a main fraction. Vpc analysis (3% XE-60 column, programmed temperature at 7.5°/min from 30°–250°, 60cc/min He flow rate) indicated this fraction to be 93% monoalkylated product, 6% starting material, and 1% dialkylated product. An analytical sample was prepared by preparative TLC on silica gel $HF_{254}$, eluting with hexane-ethylacetate 2:1 ($R_f$=0.66), followed by bulb-to-bulb distillation (105° at 1.5 mm). Vpc (3% XE-60 column at 80°, 60cc/min) showed one peak at RT 14.0 minutes.

EXAMPLE 5
trans-2-(2'-Chloropropenyl)-4-methyl-4-decen-8-ynoic acid, 32a

A solution of 0.050 mole NaOMe in 25ml MeOH was prepared by adding 1.15g (0.050 mole) of sodium to 25ml of absolute methanol. The resultant solution was heated to 50°0 under a dry nitrogen atmosphere, after which 10.33g (0.050 mole) of dimethyl 2-(2'-chloropropenyl)malonate was added rapidly. After 10 minutes, 7.85g (0.050 mole) of trans-1-chloro-2-methyl-oct-2-en-6-yne was added dropwise over 10 minutes. An immediate reaction precipitating NaCl was noted. The resultant reaction mixture was refluxed for 60 minutes. After cooling, the solution was made neutral by dropwise addition of concentrated HCl. The solvent was then evaporated, after which the residue was taken up in 50ml ether and 50ml water. The aqueous solution was washed with ether (2 × 25ml), the combined portions of which were washed with brine, dried over $MgSO_4$ and concentrated to yield 15.73g of a yellow oil. (31a) Vpc analysis (3% XE-60 column, 100°–200° programmed temperature 10°/min with delay of 4.0 min, 60cc/min He flow rate) indicated this product to be 5% starting material and 95% alkylation product. This diester was not further purified, but was saponified by refluxing for 2 hours with 15.6g KOH in 95ml water. The resultant dark solution was cooled to 0° and made acidic (pH 1) by addition of concentrated HCl. This heterogeneous mixture was extracted with $CHCl_3$ (3 × 50ml), the combined portions of which were dried over $MgSO_4$ and concentrated yielding 12.01g of a viscous brown liquid. The crude diacid was heated slowly with an oil bath, while stirring in a 25ml flask equipped with a gas bubbler. Gas evolution began at 100° and proceeded vigorously at 140°. Brief heating at 160° completed the decarboxylation. The residue was then short path distilled yielding one main fraction of 7.07g of a colorless liquid, having bp 145°–147° at 6μ. Yield 55%. Vpc analysis (3% XE-60 column at 160°, 60cc/min He flow rate) showed this product to be >95% pure.

EXAMPLE 6
trans-2-(2'-Chloro-2'-propenyl)-4-methyl-4-decen-8-ynal, 33a

A. A solution of 7.07g (27.7 moles) of trans-2-(2'-chloropropenyl)-4-methyl-4-decen-8-ynoic acid in 50ml of dry ether was added dropwise to a suspension of 1.05g (27.7 mmoles) of $LiAlH_4$ in 25ml dry ether while vigorously stirring under a dry nitrogen atmosphere. After 15 minutes, excess $LiAlH_4$ was decomposed with 50ml of 20% KOH. The resultant mixture was stirred for 15 minutes and then suction filtered through celite. The filtrate was poured into a separatory funnel and the layers spearated. The aqueous layer was extracted with ether (2 × 50ml), the combined portions of which were washed with brine, dried over $MgSO_4$ and concentrated, yielding 5.97g of a colorless liquid. Bulb-to-bulb distillation (150° at 3μ) yielded 5.85g (88%) of a colorless liquid. Vpc analysis (3% XE-60 column at 150°, 60cc/min He flow rate) showed this material to consist of >95% one component of RT 5.0 min and <5% of a volatile impurity.

B. Chromiumtrioxide-pyridine complex (3.2 mmole) was prepared by adding 3.20g (32.0 mmoles) of chromiumtrioxide to 5.2ml (64 mmoles) of pyridine in 60ml $CH_2Cl_2$. After 20 minutes, 0.96g (4.0 mmoles) of alcohol 33a .n 4ml $CH_2Cl_2$ was added followed 30 min later by the addition of 75ml ether. After washing repeatedly with 10% aq. KOH, followed by two washings with 5% aq. HCl, normal workup yielded 0.85g of a light yellow liquid. Bulb-to-bulb distillation (150° at 0.024mm) yielded 0.77g (81%) of a colorless liquid. Vpc analysis (3% XE-60 column at 130°, 60cc/min He flow rate) indicated this product to be >95% pure showing one main peak, having RT of 6.7 minutes.

EXAMPLE 7
7-Methyl-9-(2'-chloro-2'-propenyl)-nonadeca-trans, trans-6,10-dien-2-yn-15,18-dione diethylene ketal, 34a Phenyllithium-THF solution (1.14M phenyllithium) was added dropwise by syringe to a suspension of 1.77g (2.80 mmoles) of phosphonium salt (diethylene ketal of (2,5-nonadion-1yl)triphenylphosphonium iodide)(previously dried at 50° and 0.05mm for 60 minutes) in 55ml dry THF until a yellow ylid color was just observed. While rapidly stirring under dry nitrogen at room temperature, 14.1ml of 1.14M phenyllithium-THF solution (16.1 mmoles) was added quickly. The resultant deep red solution was cooled to −78° and after 10 minutes, a solution of 3.4g (14.2 mmoles) of aldehyde 33a in a total of 36ml of dry THF was added by syringe very slowly down the cold side of the flask over 15 minutes. After 5 minutes 21ml of 1.14M phenyllithium-THF solution (24 mmoles) was added dropwise down the cold side of the flask over 10 minutes. After 10 minutes, 128ml of dry ether was added down the cold flask side over 5 minutes. The deep red reaction mixture was then allowed to warm to −15° over 15 minutes, after which the reaction was quenched by addition of 1.0ml of methanol, causing the immediate formation of a white precipitate. After stirring at room temperature for 30 minutes, the solvent was evaporated and the residue triturated with hexane. Normal workup yielded 7.48g of a yellow oil. Vpc analysis (3% OV-17 column at 245°, 60cc/min He flow rate) indicated this product to be ca. 60% pure, contaminated by several volatile impurities. Only one peak of RT 11.8 min was observed for the olefinic bis ketal. No cis olefinic isomer was detected. This intermediate was not further purified.

EXAMPLE 8
2-(7'-Methyl-9'-(2''-chloro-2''-propenyl)-tridecatrans, trans-6',10'-dien-2'-ynyl-1')-3-methylcyclopent-2-enone-1, 35a To a mixture of 200ml MeOH and 60ml water was added 7.48g of ca. 60% pure bis ketal 34a. The resultant solution was degassed by bubbling nitrogen through it for 30 minutes. One ml of concentrated HCl was then added. After stirring at 48° for 9 hours, the reaction mixture was neutralized by addition of NaHCO$_3$. The reaction mixture was concentrated to a volume of ca. 50ml after which it was extracted with ether (3 × 25ml), the combined portions of which were washed with water (3 × 25ml), brine (1 × 25ml), dried over MgSO$_4$ and concentrated, yielding 6.17g of a yellow liquid. Vpc analysis (3% OV-17 column at 230°, 60cc/min He flow rate) indicated the hydrolysis to be complete, showing, in addition to some volatile impurities, only one peak of RT 6.5 minutes for the diketone. No starting material was observed. This diketone was not further purified or characterized.

The crude diketone was dissolved in 100ml MeOH. The resultant solution was degassed by bubbling argon through it for 15 minutes, after which 5.0g KOH was added. The basic solution was refluxed for 2 hours and then concentrated to a volume of ca. 20ml. Thirty ml water was added and the resultant mixture extracted with ether (3 × 25ml), the combined portions of which were washed with water (3 × 25ml), brine (3 × 25ml), dried over MgSO$_4$ and concentrated, yielding 6.16g of a light colored oil. Purification by dry column chromatography over 200g grade II basic alumina, eluting with CH$_2$Cl$_2$, followed by bulb-to-bulb distillation (220° at 5μ) yielded 1.61g of a colorless oil. This represents a 32% yield from the aldehyde 33a. Vpc analysis (3% OV-17 column at 230°, 60cc/min He flow rate) showed only one peak of RT 6.2 minutes. An analytical sample was prepared by preparative TLC on silica get HF$_{254}$, eluting with hexane-ethylacetate 4:1 (R$_f$=0.20), and then bulb-to-bulb distilled (210° at 7μ).

EXAMPLE 9
2-(7'-Methyl-9'-(2''-chloro-2''-propenyl)-tridecatrans, trans-6',10'-dien-2'-ynyl-1')-1,3-dimethyl cyclopent-2-enol-1, 36a To a solution of 140mg (0.39 mmoles) of cyclopentenone 35a in 5ml of dry ether was added 1.0ml of 1.6M methyllithiumether solution while vigorously stirring at 0° under dry nitrogen. After one hour, 5.0ml of water was cautiously added and the product isolated by ether extraction (3 × 5ml) as quickly as possible. Normal workup yielded 145mg of a colorless oil. The alcohol was stored at 0° under dry nitrogen and then used as quickly as possible.

EXAMPLE 10
trans-4,4-Dicarbomethoxy-6-methyl-dodecadien-1, 6-yn-12, 30b

A solution of 0.158 mole sodium methoxide in 150ml methanol was prepared by adding 3.64g (0.158 FW) sodium to 150ml of absolute methanol. To this solution under an argon atmosphere 27.4g (0.158 mole) 4,4-dicarbomethoxybutene-1 was added over 10 minutes with stirring. The reaction mixture was stirred at room temperature for ca. 20 minutes and then 22.5g (0.1435 mole) trans-1-chloro-2-methyloct-2-en-6-yne (bp 49°/0.25mm, containing ca. 20% of the sec.-chloro-isomer by nmr; the two isomers can easily be separated by distillation through Vigreux-column) was added over a period of 15 minutes, followed by heating to 50° for 1 hour. The reaction mixture was cooled and poured into a separatory funnel onto a mixture of ice and ca. 50ml 20% hydrochloric acid and extracted with ether. The organic layer was washed with water, saturated sodium bicarbonated solution, water, then finally dried over anhydrous magnesium sulfate. The residue obtained on removal of the solvent under reduced pressure was distilled through a short, well insulated column to give a total of 29.88g (71% yield) diester 30b in two fractions of bp 111°–116° (7.32g) and 116°–117.5° (22.56g) at 0.008mm as a colorless viscous liquid.

EXAMPLE 11
trans-2-(2'-prop-2'-enyl)-4-methyl-4-decen-8-ynoic acid, 32b (isolated as R(+)- and s(+)-α-methylbenzylammonium-salts)

Diester 30b (22.0g, 75.3 mmoles)(bp 116°–117.5°) was refluxed for 20 hours under argon in a solution of 40g (ca. 0.6 mole) potassium hydroxide in 200ml water and 200ml methanol. The reaction mixture was cooled and poured on ice, acidified with 20% hydrochloric acid and extracted with ether. The organic layer was washed with water and dried over anhydrous magnesium sulfate. The solvent was removed under reduced pressure and the very viscous residue (crude diacid) dissolved in 300ml N,N-dimethyl-formamide. This solution was refluxed for 2.5 hour (carbon dioxide was evolved immediately upon reaching reflux temperature, bariumhydroxide test), cooled, poured on ice (containing a few ml 20% hydrochloric acid) and extracted with ether. The ether solutions were washed several times with 5% hydrochloric acid and finally dried over anhydrous magnesium sulfate. The crude acid obtained on removal of the solvent under reduced pressure as a nearly colorless, viscous oil was dissolved in 50ml acetonitrile. To this solution 9.10g (75 mmoles) S(−)-α-methylbenzylamine was added. Crystallization at ca. −20° overnight gave 19.5g (76%) of S(−)-α-methylbenzylammonium salt of the acid 32b, mp 60°-65° (mixture of diastereomers) as a white solid.

The resulting mother liquid was concentrated under reduced pressure, poured on ice, acidified with dilute hydrochloric acid and extracted with ether. The ether layer was washed three times with dilute acid, dried over anhydrous magnesium sulfate, and evaporated to give 4.1g (ca. 18.5 mmoles) of crude free acid 32b. Acetonitrile (30ml) and 2.25g (18.5 mmoles) R(+)-α-methylbenzylamine were added. Crystallization at 0° for several hours gave 3.98g (15.5%) R(+)-salt, mp 70°-75° (mixture of diastereomers). The structure and purity of both salt mixtures was confirmed by nmr. Total yield: 9.15%

The diastereomeric mixtures of the ammonium salts, obtained as described above, were recrystallized several times from acetonitrile to a constant melting point of 83°-86°. The appearance of the material changed from white solid to long shiny needles. Three to five recrystallizations were usually required. For the last crystallizations diisopropylether or hexane is suitable as a solvent as well.

The four isomeric α-methylbenzylammonium salts of the acid 32b had the following properties:
R(+)-α-methylbenzylammonium salt of the (+)-acid: mp 83°-86°, $[\alpha]_D^{20}$ (CHCl$_3$, 100mg/ml + 5.15°; S(−)-α-methylbenzylammonium salt of the (−)-acid 32b: mp 83°-86°, $[\alpha]_D^{20}$(CHCl$_3$, 100mg/ml) −5.46° (another sample, mp 83°-86° showed −5.26°); R(+)-α-methylbenzylammonium salt of the (−)-acid 32b: mp 63°-64°, $_D^{20}$ (CHCl$_3$, 100mg/ml) + 11.75° (white needles) S(−)-α-methylbenzylammonium salt of the (+)-acid 32b: mp .63°-64°, $[\alpha]_D^{20}$ (CHCl$_3$, 100mg/ml) −11.30° (white needles).

EXAMPLE 12 (−)-acid,
(−)-trans-2-(2'-propenyl)-4-methyl-4-decen-8-ynal, 33b

A. S(−)-α-Methylbenzylammonium salt of the (−)-acid (mp 83°-86°, $[\alpha]_D^{20.9}$ −5.46°) (3.415g, 10 mmoles) was added to a mixture of ca. 75g ice and 25ml 20% hydrochloric acid in a separatory funnel. This mixture ws shaken vigorously for 5 minutes and then extracted with ether (general procedure to liberate the free acid from the ammonium salts). The organic phase was washed twice with water, dried over anhydrous magnesium sulfate and the solvent removed under reduced pressure to yield the acid 32b as an almost colorless oil. $[\alpha]_D^{20.9}$ (1M in CCl$_4$) = −3.06°.

The crude acid was dissolved in 100ml ether and added dropwise at 0° to a stirred slurry of 1.5g lithium aluminium hydride in 50ml ether. The reaction mixture was allowed to warm to room temperature and stirred overnight. Excess reagent was destroyed with water-saturated ether at 0°. After this, the reaction mixture was poured on ice and hydrochloric acid and extracted with ether. The organic phase was washed with 5% potassium hydroxide solution, twice with water and dried over anhydrous magnesium sulfate and concentrated under reduced pressure. Kugelrohr-distillation of the residue (150°/0.008mm) gave 2.009g (98% yield) alcohol as a colorless liquid $[\alpha]_D^{20}$ (neat) = −0.453°.

B. To a solution of 9.6g (120 mmoles) dry pyridine in 100ml dry dichloromethane (treated with conc. sulphuric acid and filtered through alumina (Woelm basic, activity grade I) immediately before use) was added 3.6g (36 mmoles) chromium trioxide all at once under vigorous stirring at room temperature (after a few minutes, the reaction mixture turns dark purple). After one hour, a solution of 1.034g (5.0 mmoles) (+)-alcohol prepared as described above (derived from (+)-acid, $[\alpha]_D^{20}$ (neat) = +0.576°) in ca. 2ml dichloromethane was added quickly. A black precipitate was formed immediately. After 10 minutes the dichloromethane layer was poured onto a mixture of ice and 200ml water. The black residue was washed twice with dichloromethane. The combined layers were shaken vigorously for 5 minutes in a separatory funnel and then the organic phase separated. The aqueous layer was extracted twice with dichloromethane. The combined extracts were dried over anhydrous magnesium sulphate and the solvent removed under reduced pressure at room temperature. The residue was filtered through 20g alumina (Woelm, neutral, activity grade III, dichloromethane) to give after removal of the volatile components at 25°/0.05mm/1 hr 859mg (83% yield) aldehyde 33b.

EXAMPLE 13
7-Methyl-9-(2'-propenyl)-nonadeca-trans, trans-6,10-dien-2-yn-15,18-dione, bis ethylene ketal, 34b Under an argon atmosphere 0.75M phenyllithium ethereal solution was added dropwise by syringe at room temperature to a stirred suspension of 3.8g (6 mmoles) of phosphonium salt (see Ex. 7) in 30ml THF until a yellow ylid color was observed. Ca. one ml was required.

While rapidly stirring at room temperature, 8.0ml 0.75M PhLi ethereal solution (6 mmoles) was added quickly. The resultant orange-red solution was cooled to −78° and after 10 minutes a solution of 1.12g (5.48 mmoles) aldehyde 33b in 10ml THF was added by syringe very slowly down the cold side of the flask over 15 minutes. After 5 minutes, 30ml of dry ether was added likewise over 5 minutes. The deep orange-red reaction mixture was then allowed to warm up to −15° over 15 minutes, after which the reaction was quenched by addition of 2ml methanol. The light yellow reaction mixture was poured on ice and extracted with ether. The organic layer was washed 3x with saturated NaHCO$_3$ solution, dried over anhydrous K$_2$CO$_3$ and the solvents removed under reduced pressure. The residue was filtered through 20g alumina (Woelm, basic, activity grade III, hexane-ether 1:1 (vol), ca. 150ml) to yield after concentration a hexane-ether soluble oil, which was purified by chromatography on 150g aluminium oxide (basic, activity grade III), eluting first with hexane and then with 10% ether-hexane to yield the desired bis ethylene ketal 34b. Kugelrohr-distillation (ca. 200°/0.006mm) gave 1.258g (51% yield) 34b as a colorless liquid.

EXAMPLE 14
2-(5'-(2"-propenyl)-7'-methyl-trideca-trans, trans-3',7'-dien-12'-yn-1-yl)-3-methyl-cyclopent-2-en-1-one, 35b The suspension of 1.080g (2.51 mmoles) bis ethylene ketal 34b and 70ml of a methanol-water-conc. hydrochloric acid solution (300:90:1 by volume) was stirred at room temperature (a solution is formed after ca. 4 hour) for 20 hour. The reaction mixture was poured on ice and extracted with ether. The ether solutions were washed (3 × H$_2$O), dried over anhydrous magnesium sulfate, followed by removal of the solvent under reduced pressure. The oily residue was dissolved in 70ml 5% potassium hydroxide (approx. 85%) in absolute methanol. This solution was refluxed under argon for 2 hour, allowed to cool to room temperature and stirred overnight. The yellow reaction mixture was poured on ice and extracted with ether. The organic layers were washed three times with water and dried over anhydrous potassium carbonate. Concentration under reduced pressure and Kugelrohrdistillation (ca. 190°/0.02mm) gave 810mg (99.5%) 35b as a colorless oil. Vpc-analysis (OV-17, 199°) indicated less than 0.5% of the cis-isomer.

EXAMPLE 15 3-Methyl-11 α-(2'-chloroprop-2'-enyl)-A-nor-3-pregnen-20-one, 40a (j,g=Me, e = 2-Cl-allyl)

Trifluoroethanol (TEE) (8.0ml) (dried over active molecular sieves type 3A) was added to 145mg (0.39 mmole) of cold 36a. The resulting mixture was cooled to 0° and an inert atmosphere provided by passing dry nitrogen over it for 5 minutes, after which 0.32ml (4.0 mmoles) of dry trifluoroacetic acid (TFA) was added dropwise over 5 minutes. After 3 hours at 0°, 2ml water and 8ml ether were added and after 15 minutes, normal workup yielded 148mg of a dark oil. Vpc analysis (3% OV-17 column at 230°, 60cc/min He flow rate) showed, in addition to several volatile impurities, peaks of RT's 6.9 and 7.6 minutes for the 17α and 17β isomers of the named compound. Preparative TLC of the crude product on silica gel HF$_{254}$, eluting with hexane-ethyl acetate 4:1, yielded 43mg of a light yellow oil. This material was estimated to be ca. 75% pure by TLC, thus indicating a yield of 21%.

EXAMPLE 16
A-nor-11-(2'-propenyl)-3-methyl-3-pregnen-20-one, 40b a. General procedure for enone 35b → allylic cyclopentenol 36b Enone 34b (222mg, 0.685 mmoles, 94.5% pure, >99% trans) was dissolved in 25ml dry ether and cooled to 0°. Then 2.0ml methyllithium solution (Ventron, ca. 1.7M, 3.4 mmoles) was added at once. Excess methyllithium was destroyed after 10 minutes by adding water-saturated ether at 0°. Ice (ca. 5g) was added to the reaction mixture and the flask shaken until the organic layer became clear. The ether phase was decanted and filtered through anhydrous potassium carbonate directly into the cylindric reaction flask, precooled to 0°, under an argon atmosphere. The ether was removed at water pump pressure below 0° (ice bath, ca. 40 minutes).

b. Cyclization 36b→40b (j,g=Me, e = allyl) (TFE-TFA 5.2 (vol) 0°, 4 hr. 22 hr).

To the flask containing the above-mentioned sample of 36b was added 50ml 2,2,2-trifluoroethanol by syringe slowly down the flask. The milky mixture was stirred and degassed for 20 minutes and then 20ml trifluoroacetic acid was added over 3 minutes. The white milky mixture turned orange immediately on adding the acid and became a solution after ca. 5 minutes.

After 4 hour at 0°, 10ml was taken out of the reaction mixture by syringe and poured on a mixture of ice and excess sodium bicarbonate solution (orange color of reaction mixture disappeared). This mixture was shaken vigorously and extracted with ether. The organic layer was washed three times with saturated sodium bicarbonate solution, dried over anhydrous potassium carbonate and the solvents removed under reduced pressure to yield an orange-brown oil. Thin-layer chromatography (silica gel, hexane-20% ethyl acetate) showed one spot at R$_f$0.5 for 40b and an elongated spot at ca. R$_f$=0.6

After a total of 22hr/0° (ice bath) the remainder of the reaction mixture was worked up in the same way. The nmr-spectrum of the obtained crude product was nearly identical to that of the 4hr/0°-product.

Purification by chromatography on a Florisilalumina-Florisil-column gave 106mg (53% yield, not distilled) 40b.

In another run carried out under nearly identical conditions, (300mg enone 35b (0.925 mmoles) converted into 40b as described above, has cyclized in 70ml TFE-20ml TFA at 0°. No significant differences in nmr-spectrum and tlc could be detected in the crude products after 15min/0°; 3hr/0° and 48hr/0°. The 48hr/0°-sample was purified by chromatography and 40b obtained in 58% (chromatographed, not distilled) yield.

c. Cyclization in TFE-TFA 5:2 (vol)/0°.

Enone 34b (200mg, 0.617 mmoles, 94.5% pure, >99% trans) was converted to 36b by the above procedure. The resulting product 36b was cyclized in 50ml TFE - 20ml TFA at 0° and after workup purified by filtration through a Florisilalumina-Florisil-column (hexane-10% ether), followed by chromatography on 20g Florisil (hexane; hexane-10% ether). Kugelrohr-distillation (180°/0.006mm) gave 105mg (50% yield) 40b (very viscous, colorless oil).

d. Cyclization 36b →40b in TFE - TFA-20% water.

Enone 34b (50mg, 0.154 mmoles, 94.5% pure, >99% trans) was converted into 36b by the above procedure "a" and cyclized in 8ml TFE - 5ml TFA-20% water (same orange color appeared on adding the acid); 10 min/0°, followed by 10hr/room temperature; yield ca. 45%, nmr-spectrum showed a minor impurity at 1.23ppm.

e. Cyclization in TFE-TFA 1:1 (vol) at -5° for 15 minutes.

Enone 34b (80mg, 0.245 mmoles, 97% pure, 95.5% trans) was converted into 36b by the above procedure "a" and cyclized in 20ml TFE - 20ml TFA at -5° (iceacetone bath) over 15 minutes. Workup and purification as described above "b" gave 29mg (35% yield) 40b, which appeared to be very pure by tlc and nmr.

EXAMPLE 17
4,5-seco-11-formulmethylpregnan-3,5,20-trione 41b (g,j=Me, e' = CHOCH$_2$-)

Using a Rubin ozonizer, methylene chloride (16ml) was saturated with ozone at -78° (0.64 mmol O$_3$). This royal blue solution was transferred using positive nitrogen pressure to a solution of cyclization product 40b (98mg, 0.29 mmoles) in CH$_2$Cl$_2$ (5ml). After ten minutes at -78°, a pale blue color remained and was discharged by bubbling N$_2$ through the solution. The reaction mixture was transferred to a roundbottom flask, treated with acetic acid (5ml), zinc powder (0.6g) and stirred for 5 hours. After concentrating at reduced pressure, the residue was taken up in water and extracted three times with ether. The combined ether extracts were washed 3 times with saturated NaHCO$_3$ solution, once with brine, dried (MgSO$_4$) and concentrated to yield 71mg of an oil.

EXAMPLE 18
4,5-seco-11-carboxymethylpregnan-3,5,20-trione, 41b-1

The triketoaldehyde 41b (71mg) was dissolved in acetone (10ml), cooled to 0° and treated with excess Jones Reagent. After destroying the excess with isopropanol, the reaction mixture was concentrated at reducing pressure, acidified (ice-cold 10% HCl) and extracted three times with ether. The ether extracts were washed twice with brine, dried (MgSO$_4$) and concentrated to afford 65mg of an oil.

EXAMPLE 19
11-Carboxymethylpregn-4-en-3,20-dione, 42b

Triketoacid 41b-1 (65mg) was heated in 5% KOH-MeOH (5ml) at reflux under nitrogen for 3 hours. After cooling and concentrating at reduced pressure, the residue was partitioned between ether and water. The aqueous layer was separated, then acidified (5% HCl) and extracted three times with fresh ether. These extracts were washed with brine, dried (MgSO$_4$) and concentrated to yield 46mg of impure 42b as an oil.

EXAMPLE 20
4,5-seco-11-carboxymethylpregnan-3,5,20-trione, 41b-1 (g,j=Me, e' = HO$_2$CCH$_2$-)

Tetracyclic ketone 40a was treated with approx. 1 mol-equiv. ozone in a Rubin ozonizer (dichloromethane, -78°), worked up with Zn/AcOH, followed by A-ring cyclization of the crude triketo-acid in 5% KOH-methanol. See Examples 37 and 39. Compound 42b was obtained.

It is evident from the prior examples, that in accordance with this invention, steroids can be easily synthesized with a wide variety of substituents at the 11-position. In addition, great flexibility is provided for introducing groups in the side chain at the 17-position and providing for nor-steroids, either at the 18 or 19-position or in the A-ring. Also, the chain length at the 18 and 19-positions may be varied. The central compound is a dienyne which may have a variety of groups which are functionalized, so that upon initation with an acid catalyst, the molecule cyclizes to the steroid cyclic structure or the A-norsteroid cyclic structure. By appropriate choice of the Z group or by subsequent treatment, either the cholestane or coprostane geometry may be achieved.

The procedures employed for synthesizing the steroids introduce the proper geometry for double bonds, so that upon cyclization the natural steroid geometry is obtained. Cyclization of the polyunsaturated compound to the desired steroid product is achieved despite substantial non-bonded steric interactions which result as the molecule becomes compressed into the tetracyclic product. In addition, the acetylenic bond provides for 5-membered ring formation directly.

In accordance with this invention, the terminator fragment containing the alkenyl group has a carboxylic acid function which can be used to resolve the fragment into its two stereoisomers. The carboxyl group may then be reduced to the aldehyde, condensed with the initiator group, and upon cyclization and asymmetric induction will provide an optically active product, whichever steroisomer is desired. In addition, the olefinic group allows for a wide variety of chemical transformations. The olefinic group may be oxidized to an aldehyde or carboxylic acid group. The carboxylic acid group may be degraded further to methyl, exo-methylene, halo methyl, hydroxy methyl, or the like, by known conventional techniques. In addition, the carboxyl group may be reduced to the alcohol, dehydrated and the resulting vinyl compound oxidized to C-11 formyl, carboxy or by successive steps to hydroxy or oxo. Thus, a direct route into C-ring functionalizing compounds is provided which may be used for the preparation of corticosteroids, analogs of the corticosteroids or other C-ring functionalizing steroids.

Although the foregoing invention has been described in some detail by way of illustration and example for purposes of clarity of understanding, it will be obvious that certain changes and modifications may be practiced within the scope of the appended claims.

What is claimed is:
1. A compound of the formula:

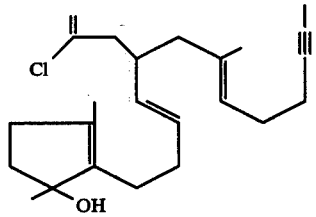

2. A compound of the formula:

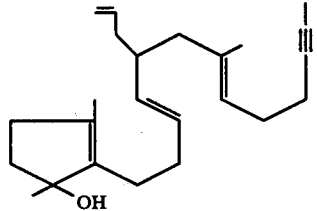

* * * * *